US006650937B2

United States Patent
Kerver (10) Patent No.: US 6,650,937 B2
(45) Date of Patent: Nov. 18, 2003

(54) METHOD AND SYSTEM FOR GRADUAL CARDIAC TRAINING USING AN IMPLANTABLE MEDICAL DEVICE

(75) Inventor: Harry B. A. Kerver, Duiven (NL)

(73) Assignee: Medtronic, Inc., Minneapolis, MN (US)

( * ) Notice: Subject to any disclaimer, the term of this patent is extended or adjusted under 35 U.S.C. 154(b) by 153 days.

(21) Appl. No.: 09/844,069

(22) Filed: Apr. 30, 2001

(65) Prior Publication Data

US 2002/0082664 A1 Jun. 27, 2002

Related U.S. Application Data

(63) Continuation-in-part of application No. 09/705,804, filed on Nov. 6, 2000.

(51) Int. Cl.$^7$ .............................................. A61N 1/365
(52) U.S. Cl. .......................................... 607/9; 607/17
(58) Field of Search .................................. 607/9, 17

(56) References Cited

U.S. PATENT DOCUMENTS

| | | | | |
|---|---|---|---|---|
| 4,878,497 A | * | 11/1989 | Callaghan et al. | ............. 607/9 |
| 5,944,743 A | | 8/1999 | Janssens | ........................ 607/9 |
| 6,238,422 B1 | * | 5/2001 | Van Oort | ..................... 607/25 |

OTHER PUBLICATIONS

Janssens, "Pacemaker with programmable rate variation for treatment of patients following ablation of the atrio–ventricular junction," approved Sep. 11, 1996.

Peters et al., "Bradycardia dependent QT prolongation and ventricular fibrillation following catheter ablation of the atriovenricular junction with radiofrequency energy," Pace, Jun. 1994, p. 108–112, vol. 17.

Geelen et al., "New observations on the problem of the ventricular fibrillation and sudden death after radiofrequency ablation of the atrioventricular junction," Pace, Apr. 1996, p. 582, abstract #65, vol. 19.

P–4912 (V–0505) Letter titled "Pacemaker with Programmable Rate Variation for Treatment of Patients Following Ablation of the Atrio–Ventricular Junction"; (Author Hervé Janssens; Dated May 21, 1996, 2 pp.).

Article titled "Bradycardia Dependent QT Prolongation and Ventricular Fibrillation Following Catheter Ablation of the Atrioventricular Junction with Radiofrequency Energy"; (Author Geelen et al.; Dated Jun. 1994; Pace, vol. 17, pp. 108–112).

Abstract #65 titled "New Observations on the Problem of Ventricular Fibrillation and Sudden Death after Radiofrequency Ablation of the Atrioventricular Junction"; (Author Geelen et al.; Dated Apr. 1996; Pace, vol. 19, p. 582).

P–4517 Memo titled "Time Adaptive AVD"; (Author Chester Struble and Henri Heynen; Dated Jan. 17, 1996; 2 pp.).

Struble, "Time adaptive AVD," approved Apr. 11, 1996.

* cited by examiner

Primary Examiner—Carl Layno
(74) Attorney, Agent, or Firm—Thomas F. Woods; Eric R. Waldkoetler; Tom G. Berry (57) ABSTRACT

A method and system for pacing cardiac tissue is provided. An implantable medical device is implanted having an initial pacing function value based on a current cardiac rate of the cardiac tissue at implantation. A target pacing function value, a training increment and a training period are determined. The initial pacing function value is gradually increased to the target pacing function value by the training increment during the training period.

39 Claims, 7 Drawing Sheets

METHOD AND SYSTEM FOR GRADUAL CARDIAC TRAINING USING AN IMPLANTABLE MEDICAL DEVICE

RELATED PATENT APPLICATION

This patent application is a continuation in part of, and claims priority and other benefits from U.S. patent application Ser. No. 09/705,804 entitled "Method and System for Increasing a Pacer Function of an Implantable Medical Device Disposed within a Mammalian Heart" to Kerver filed Nov. 6, 2000, and incorporates the entirety of same by reference herein.

FIELD OF THE INVENTION

The present invention relates to the field of implantable medical devices. More particularly, the present invention relates to cardiac pacing systems that provide a method for gradually increasing a pacing function from an initial value to a target pacing function value in an implantable medical device.

BACKGROUND OF THE INVENTION

Implantable pulse generators (IPGs or pacemakers) with rate control are well known in the art. Rate control is usually accomplished using one or more rate responsive sensors to sense a parameter such indicative of the level of patient activity such as Q-T interval, exercise and the like. On the basis of the sensed parameter a desired pacing rate is set so that the cardiac demand of the patient may be met. Accordingly, such pacemakers typically employ algorithms to convert sensed parameters into a pacing rate such that a sensed increase in patient activity results in a higher pacing rate.

Certain IPGs may also be programmed with data relating to pacing rate. For example, values for a lower pacing rate limit and for an upper pacing rate limit may be programmed into an IPG. Such IPGs are typically referred to in the art as "rate responsive IPGs", and may have a variable pacing rate which changes depending on cardiac conditions such the cardiac workload of a patient. Initial parameter settings for such rate responsive IPGs are often based on clinical experience in combination with patient specific parameters such as age, lifestyle, health and so on.

Some IPG functions may be set to be automatically adjusted according to a patient's changing needs. In some cases, and especially in patients who have had their rate responsive IPGs replaced, a "Fast Learn" procedure may be employed where the patient performs a predetermined exercise and the results of the exercise are used to set IPG rate response parameter settings individualized to the patient's particular needs and condition. Parameters for an IPG's pacing rates may also be set subsequent to implantation, such as before the patient is dismissed from the hospital or during a follow up visit.

Increases in the pacing rate of the heart are often required in patients who receive IPGs. It is frequently desired to increase the heart rate of a patient suffering from bradycardia whose heart is beating at a rate that is too slow. In such cases, an IPG may be implanted to restore the patient's heart rate to a normal level. It has been discovered, however, that an immediate increase in the pacing rate of a heart in a patient suffering from bradycardia can lead to problems such as patient discomfort. At least in the case of patients suffering from bradycardia, these problems have their roots in the fact that over a period of years a patient's heart may have become accustomed to beating at a slow rate, and the heart does not respond well to suddenly being forced to beat at a higher rate.

Thus, a need exists in the medical arts for adjusting the pacing of a patient's heart in a gradual or incremental manner so that a pacing rate may be increased gradually to a target value.

Some methods have been proposed in the prior art for gradually adjusting the pacing rate of a heart. For example, U.S. Pat. No. 5,944,743 to Janssens discloses a pacemaker system for enabling special rate control for patients who have specially recognized conditions, such as patients who have undergone cardiac ablation procedures and who are particularly susceptible to bradycardia-dependent ventricular fibrillation or other arrhythmias. In such patients, the heart is typically paced at a high start value and brought down to a predetermined lower rate limit. The most pertinent prior art patent known of the present time is shown in the following table:

TABLE 1

| Prior Art Patent | | |
|---|---|---|
| U.S. Pat. No. | Date | Inventor(s) |
| 5,944,743 | Aug. 31, 1999 | Janssens et al. |

The patent listed in Table 1 is hereby incorporated by reference herein in its entirety. As those of ordinary skill in the art will appreciate readily upon reading the Summary of the Invention, the Detailed Description of the Preferred Embodiments and the claims set forth below, at least some of the devices and methods disclosed in the patent of Table 1 may be modified advantageously in accordance with the teachings of the present invention.

SUMMARY OF THE INVENTION

The present invention is therefore directed to providing a method and system for gradually increasing the rate at which pacing pulses are delivered to a patient's heart after the patient has received an IPG. The system of the present invention overcomes at least some of the problems, disadvantages and limitations of the prior art described above, and provides a more efficient and accurate means of gradually increasing the rate at which a heart is paced in a cardiac pacing system.

The present invention has certain objects. That is, various embodiments of the present invention provide solutions to one or more problems existing in the prior art respecting the pacing of cardiac tissue. Those problems include, without limitation: (a) patients experiencing discomfort after undergoing an implant procedure where an IPG is implanted to remedy slow heart rates; (b) patients' hearts suddenly being forced by implantable cardiac stimulators to beat at rates which are excessive; (c) applying initial pacing rates to patients which are uncomfortably high or excessive; (d) difficulty in determining an appropriate initial pacing rate for a particular patient, and (e) difficulty in determining a final target pacing rate for a particular patient.

In comparison to known pacing techniques, various embodiments of the present invention provide one or more of the following advantages: (a) increasing patient comfort following a pacemaker implant; (b) "training" the heart in an optimal fashion after a pacemaker implant so that the heart becomes accustomed to beating at rates higher than those attained prior to the implant, and (c) fewer patient complaints or returns to hospital following the implant of an IPG.

Some embodiments of the present invention include one or more of the following features: (a) an IPG capable of providing electrical stimuli to a patient's cardiac tissue at a rate which is time-dependent such that the average or mean rate at which pacing stimuli are applied to cardiac tissue increases gradually over a predetermined training period; (a) methods corresponding to (a) of applying such gradually increasing pacing rates to a heart following an IPG implant; (c) methods corresponding to (a) of operating an IPG to permit an initial value of a pacing rate to be determined, permitting a target value of a pacing rate to be determined, and permitting a target pacing value to be attained by a training increment during a training period.

At least some embodiments of the present invention involve determining an initial value of a pacing rate. A target value of the pacing rate is then determined. The initial value of the pacing rate is increased to the target value by a training increment during a training period. Cardiac tissue may be paced initially at a rate determined by the initial value of the pacing rate. The length of the training period may be varied according to the desires of the attending physician, in response to the detection of certain conditions, or in response to the fulfillment of predetermined criteria. A calculated value of the pacing rate function may then be determined based on a determined training increment. The cardiac tissue may be paced at the initial calculated value of the pacing rate, and the pacing rate increased according to the determined training increment.

BRIEF DESCRIPTION OF THE DRAWINGS

The above, and other objects, advantages and features of the present invention will be more readily understood from the following detailed description of the preferred embodiments when considered in conjunction with the drawings, in which like reference numerals indicate identical structures throughout the several views, and wherein.

DETAILED DESCRIPTION OF THE PREFERRED EMBODIMENTS

It is to be understood that the terms "IPG" and "IMD", as employed in the specification and claims hereof, means an implantable medical device capable of delivering electrical stimuli to cardiac tissue, and includes within its scope pacemakers, PCDs, ICDs, etc.

Figure 1:
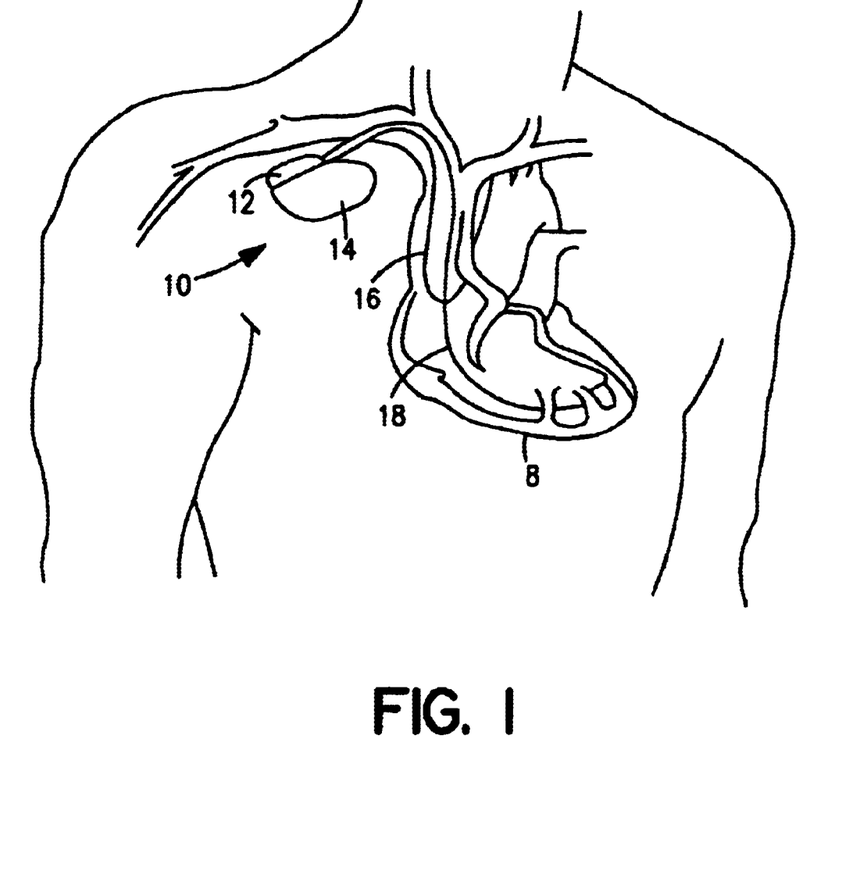
FIG. 1 is a schematic view of one embodiment of an implantable medical device in situ, made in accordance with the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all of which are hereby incorporated by reference herein, each in its respective entirety.

Figure 2:
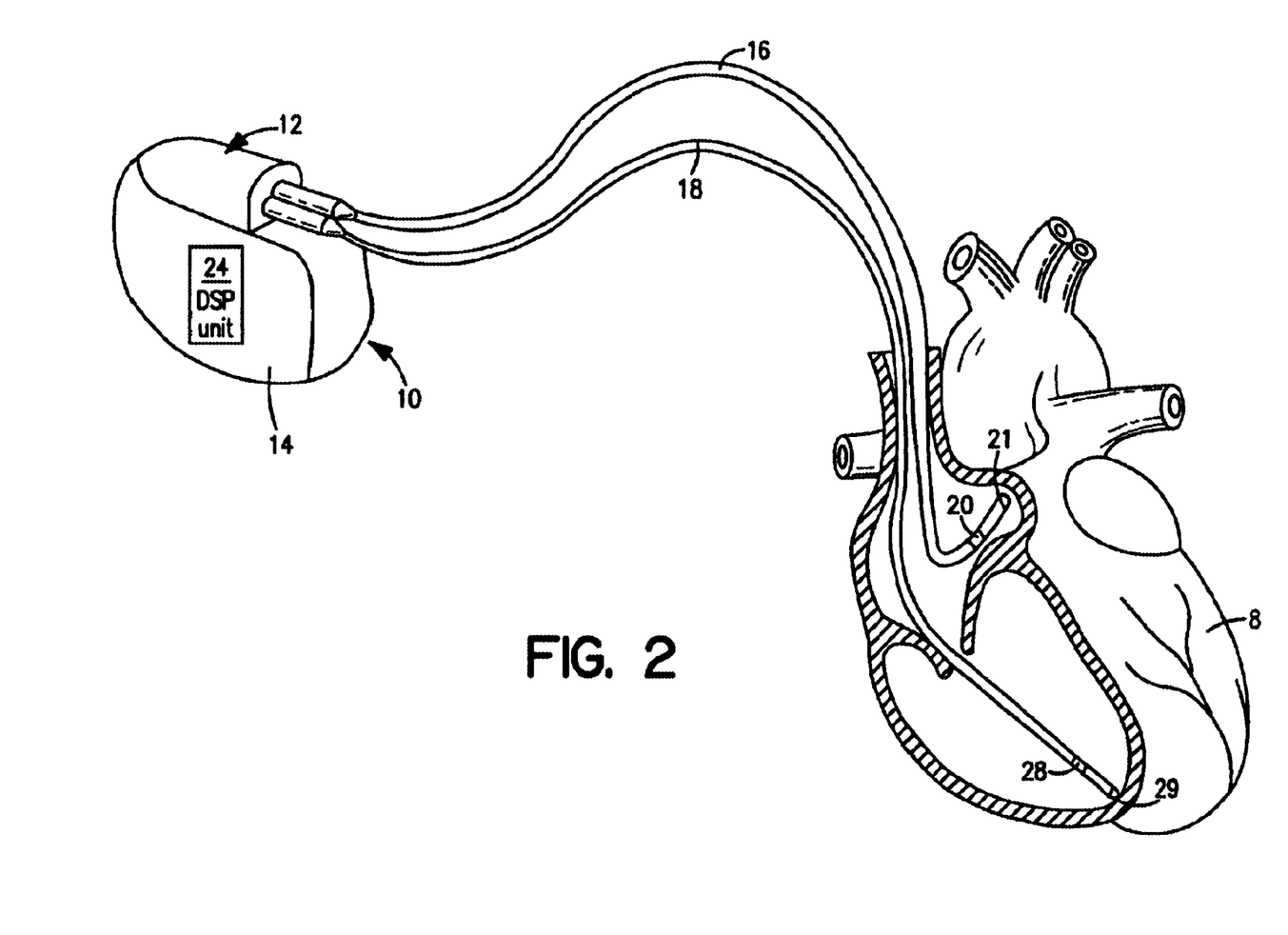
FIG. 2 is another schematic view of an embodiment of the implantable medical device of FIG. 1, made in accordance with the present invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
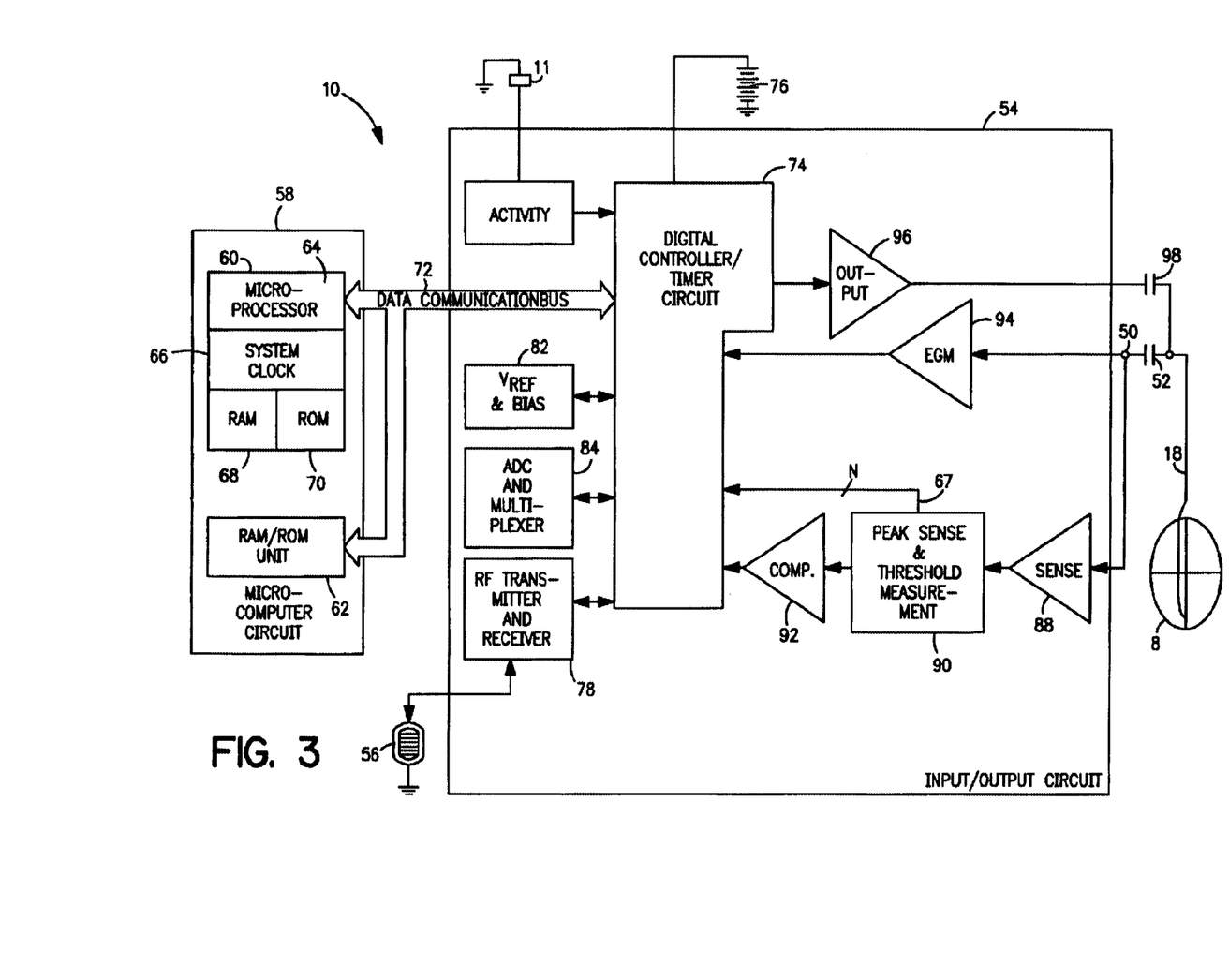
FIG. 3 is a block diagram illustrating components of an embodiment of the implantable medical device of FIG. 1, made in accordance with the present invention.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor or accelerometer 11, which may be an accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 may be programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in U.S. Pat. No. 5,312,453 to Wyborny et al. is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 may be attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. Accordingly, the rate at which heart 8 is stimulated or beats spontaneously without stimulation may be controlled and/or monitored using software-implemented algorithms or pacing rate functions stored in microcomputer circuit 58.

Microcomputer circuit 58 may comprise on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 may include microprocessor 64, system clock circuit 66 and on-board RAM 68 and ROM 70. Off-board circuit 62 may comprise a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063, issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 may generate stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data communication bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 may be coupled to sensing circuitry, including sense amplifier 88, peak sense and threshold measurement unit 90 and comparator/threshold detector 92. Circuit 74 may further be coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMDs comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMDs. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCDs. Various embodiments of the present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all of which are hereby incorporated by reference herein, each in its respective entirety.

Figure 4:
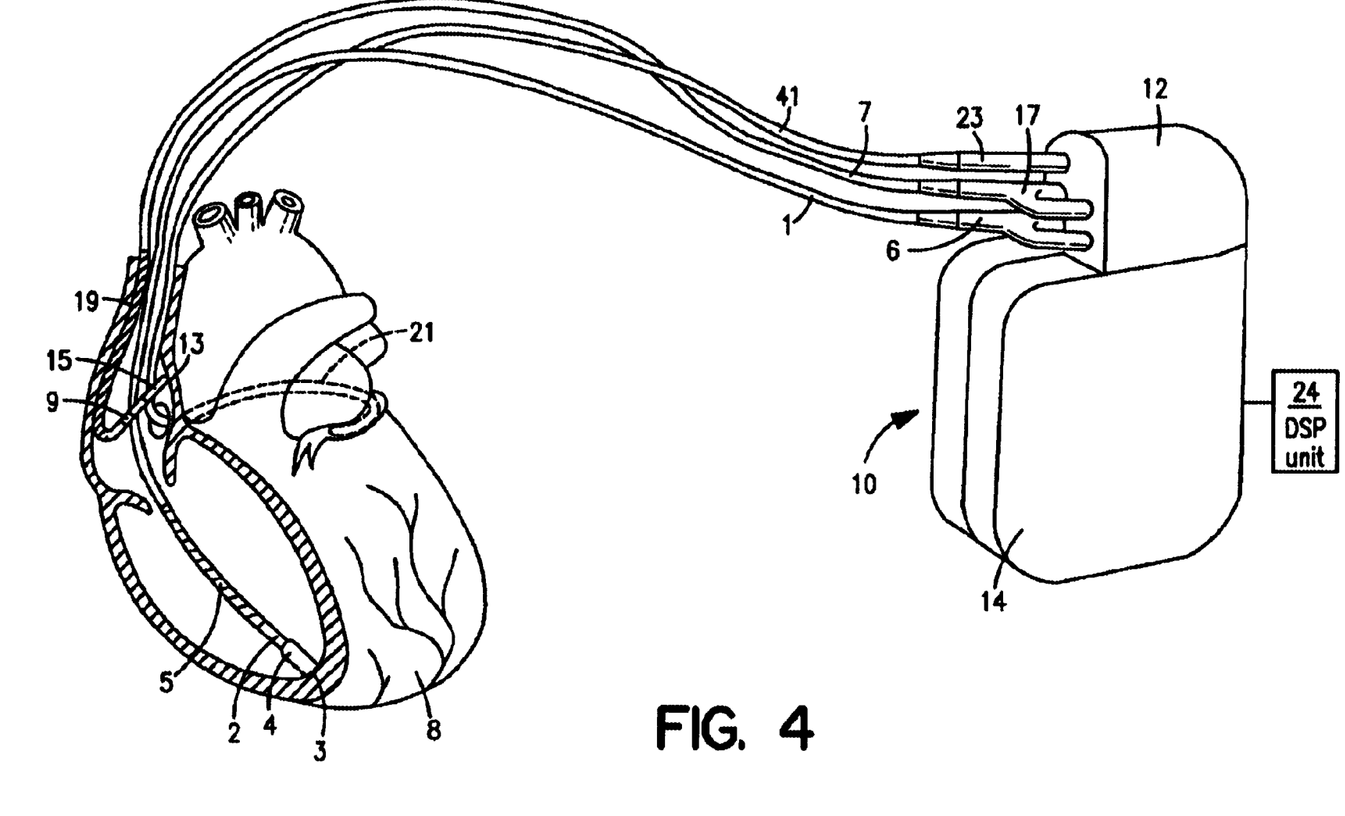
FIG. 4 is a schematic view of another embodiment of an implantable medical device, made in accordance with the present invention.
Figure 5:
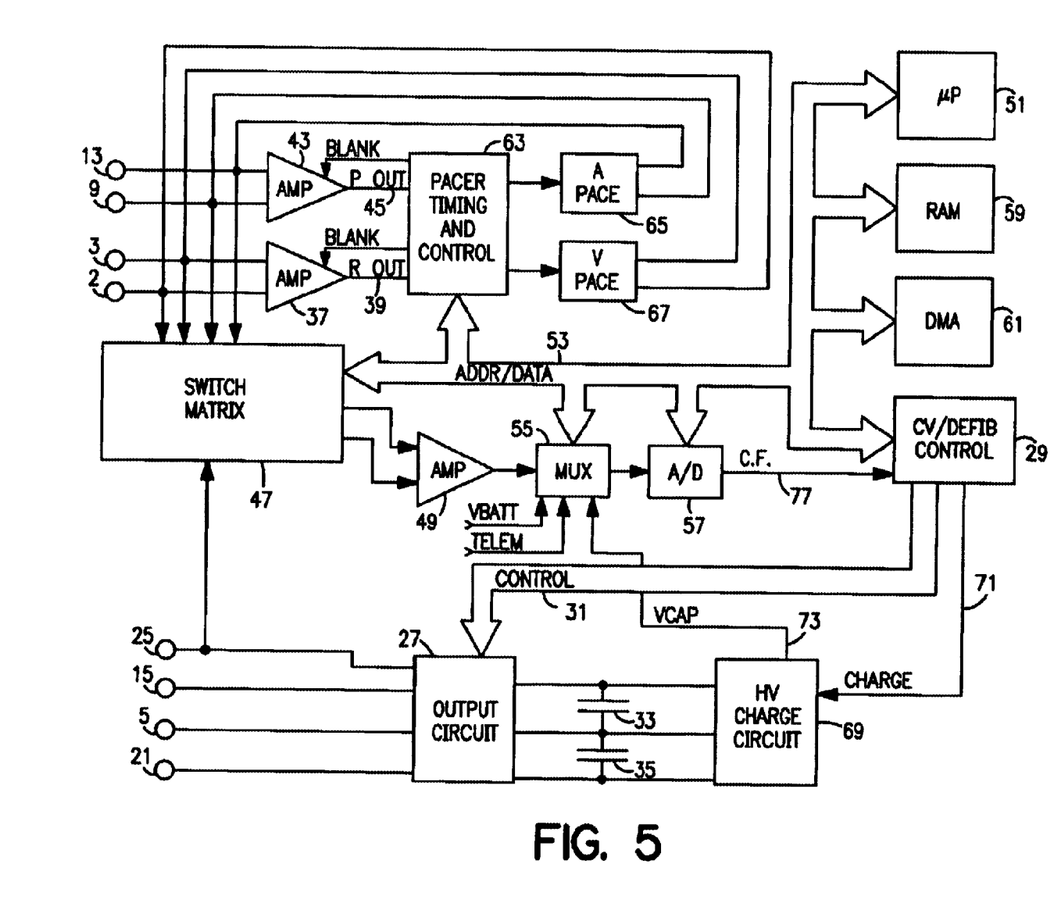
FIG. 5 is a block diagram illustrating components of an embodiment of the implantable medical device of FIG. 4, made in accordance with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 may be employed for cardiac pacing and for sensing ventricular depolarizations. At the proximal end of the lead is bifurcated connector 6, which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 may be employed for atrial pacing and for sensing atrial depolarizations. Elongated coil electrode 19 is provided proximal to electrode 9 and coupled to the third conductor within lead body 7. In one embodiment of the invention, electrode 19 is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17, which carries three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and the great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other than those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which may take the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which may also take the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention, may correspond to circuitry known to those skilled in the art. The following exemplary apparatus is disclosed for accomplishing pacing, cardioversion and defibrillation functions. Pacer timing/control circuitry 63 may include programmable digital counters which control the basic time intervals associated with DDD, VVI, DVI, VDD, AAI, DDI and other modes of single and dual chamber pacing well known to the art. Circuitry 63 also may control escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 may operate as an interrupt driven device, and may be responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts. Detection of atrial or ventricular tachyarrhythmias, as employed in the present invention, may correspond to any of the various tachyarrhythmia detection algorithms presently known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005, issued to Pless et al. and U.S. Pat. No. 4,830,006, issued to Haluska et al., all hereby incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are hereby incorporated by reference herein, each in its respective entirety.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are hereby incorporated herein by reference, each in its respective entirety, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy, microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., all of which are hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all of which are hereby incorporated by reference herein, each in its respective entirety, may also be employed.

Continuing to refer to FIG. 5, delivery of cardioversion or defibrillation pulses may be accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches, which control whether electrodes are coupled together during delivery of the pulse. Alternatively, electrodes intended to be coupled together during the pulse may simply be permanently coupled to one another, either exterior to or within the interior of the device housing, and polarity may similarly be pre-set, as in current implantable defibrillators. An example of output circuitry for delivery of biphasic pulse regimens to multiple electrode systems may be found in U.S. Pat. No. 4,953,551, issued to Mehra, and in U.S. Pat. No. 4,727,877, both of which are hereby incorporated by reference herein in its entirety.

An example of circuitry that may be used to control delivery of monophasic pulses is disclosed in U.S. Pat. No.

5,163,427 to Keimel, also hereby incorporated by reference herein in its entirety. Output control circuitry similar to that disclosed in U.S. Pat. No. 4,953,551 to Mehra et al. or U.S. Pat. No. 4,800,883 to Winstrom, both incorporated by reference, each in its respective entirety, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
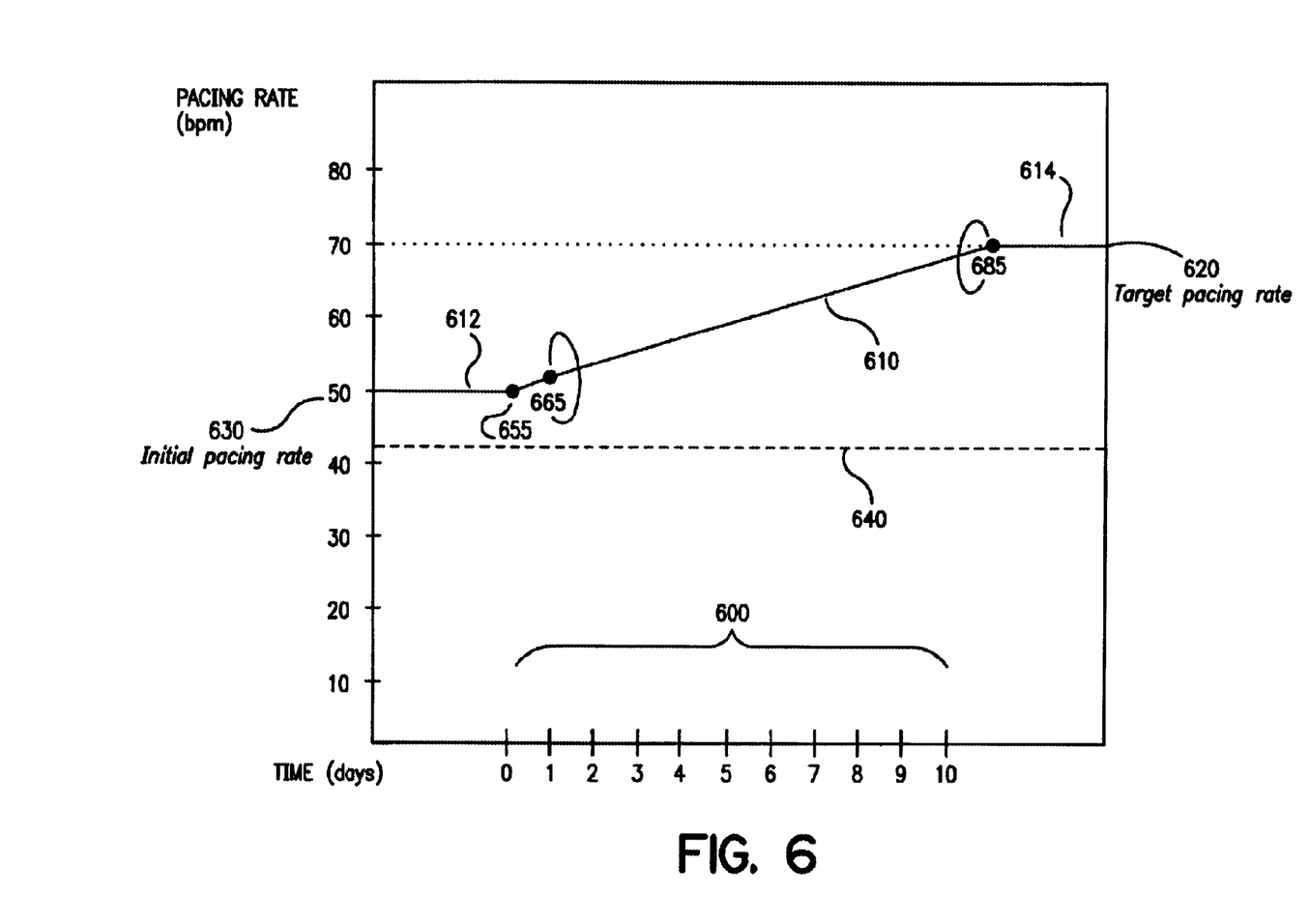
FIG. 6 is a graph illustrating one embodiment of a pacing function being increased in accordance with the presenting invention.

FIG. 6 shows a graph illustrating the operation of one embodiment of the present invention, where a pacing rate delivered by IMD 10 disposed within mammalian heart 8 is increased gradually over time period 600. In one embodiment of the present invention, a gradual increase in pacing rate is employed to gradually "train" and accustom heart 8 to be paced at ever increasing and higher pacing rates, while at the same time avoiding the discomfort and other problems that may be associated with attempting to pace heart 8 at relatively fast initial rates.

Time period 600 is the period of time over which the one or more pacing rates of the present invention are ramped up or gradually increased from an initial value to a final value, and thus may properly be characterized as a training period during which heart 8 is brought from an initial pacing rate to a final or nominal pacing rate. Time period 600 shown in FIG. 6 is ten days, but also may range, without limitation, between about 1 day and about 6 months, between about 2 days and about 4 months, between about 4 days and about 2 months, between about 5 days and about 6 weeks, between about 7 days and about four weeks, and between about 10 days and about 20 days.

In FIG. 6, the operation of a pacing rate function is represented by pacing rate function 610, which may include provisions for determining, setting and/or implementing a lower rate limit function (i.e., the lowest rate at which a patient's heart is permitted to be paced), an upper rate limit function (i.e., the highest rate at which a patient's heart is permitted to be paced), or both lower and upper rate limit functions (i.e., pacing rate function 610 may comprise both upper and lower rate limit functions).

Accordingly, in one embodiment of the present invention a lower rate limit function may be included in pacing rate function 610 such that the lowest rate at which pacing rate function 610 may be implemented increases gradually over time. A corresponding upper rate limit function may also be included in pacing rate function 610 to set or determine a maximum permitted pacing rate that gradually increases with respect to time. Thus, pacing rate function 610 may implement an upper rate limit and lower rate limit pacing functions that result in a gradually increasing maximum pacing rate along with a corresponding gradually increasing lower rate limit pacing function. Pacing rate function 610, lower rate limit pacing function 612 and upper rate limit pacing function 614 may be adjusted, controlled and implemented using software-implemented algorithms stored in microcomputer circuit 58.

Preferred lower rate limits suitable for use in the present invention range between about 25 beats per minute (bpm) and about 75 beats ppm, more preferably range between about 30 bpm and about 70 bpm, more preferably yet range between about 35 bpm and about 65 bpm, and most preferably range between about 50 bpm and about 65 bpm. Preferred upper rate limits suitable for use in the present invention range between about 30 beats per minute (bpm) and about 120 beats ppm, more preferably range between about 50 bpm and about 120 bpm, more preferably yet range between about 70 bpm and about 120 bpm, and most preferably range between about 90 bpm and about 120 bpm.

The various rates at which pacing rate function 610, lower rate limit pacing function 612, and/or upper rate limit pacing function 614 permit pacing rates to increase may be determined initially by the settings of the software-implemented algorithms associated therewith, may be determined on the basis of data gathered or acquired by IMD 10, may be preprogrammed, or may be set by the attending physician. By way of example, pacing rate function 610, lower rate limit pacing function 612, and/or upper rate limit function 614 may increase in linear, non-linear, step-wise, asymptotic, logarithmic, exponential and/or geometric fashion, or in any suitable combination or permutation of the foregoing.

It is important to note that FIG. 6 illustrates merely one embodiment of the present invention, and is not intended the limit the scope of the present disclosure or claims to that which is presented therein. Upon reading the specification and reviewing the drawings hereof, it will become immediately obvious to those skilled in the art that myriad other embodiments of the present invention are possible, and that such embodiments are contemplated and fall within the scope of the presently claimed invention.

As seen in FIG. 6, initial pacing rate 630 of pacing rate function 610 may be predetermined and stored in a memory of microcomputer 58, set by the attending physician, determined on the basis of diagnostic data gathered or sensed by IMD 10, external diagnostic means or a physician, and/or determined by comparison to a database or look-up table comprising singular values or ranges of values of initial value 630 that have been determined to be acceptable and that are stored in microcomputer 58. Similar procedures and means may be employed and implemented when determining initial values for lower pacing rate limit 612 and upper pacing rate limit 614. Preferred values for initial pacing rate 630 range between about 25 bpm and about 75 beats ppm, more preferably range between about 30 bpm and about 70 bpm, more preferably yet range between about 35 bpm and about 65 bpm, and most preferably range between about 50 bpm and about 65 bpm.

In one embodiment of the present invention, initial pacing rate 630 is determined by assessing the rate at which heart 8 beats when no electrical stimulation is provided thereto (i.e., the unpaced heart rate). In FIG. 6, the unpaced heart rate is indicated by line 640. As shown in FIG. 6, initial pacing rate 630 may be greater than the unpaced heart rate. Alternatively, initial pacing rate 630 may be less than or equal to the unpaced heart rate. As shown in FIG. 6, pacing function 610 preferably operates to increase the heart rate from initial pacing rate 630 to target pacing rate 620 over time period 600.

One or more target pacing rates 620 are preferably provided in accordance with the present invention. As shown in FIG. 6, target pacing rate 620 of 70 bpm is the "final" pacing rate achieved after the training process has been completed and heart 8 is being paced at nominal rates. In the embodiment of the present invention illustrated in FIG. 6, target pacing rate 620 corresponds to a lower rate limit for IMD 10. In other embodiments of the present invention, such as those preferably employed in rate-responsive implantable stimulators, target pacing rate 620 may correspond to an upper rate limit, a lower rate limit, or some combination of lower and upper rate limits. Preferred values for target pacing rates of the present invention range between about 25 bpm and about 160 bpm, more preferably between about 30 bpm and about 140 bpm, more preferably yet between about 40 bpm and about 120 bpm, and most preferably between about 60 bpm and about 120 bpm.

One or more target pacing rates 620 may be predetermined and stored in a memory of microcomputer 58, set by the attending physician, determined on the basis of diagnostic data gathered or sensed by IMD 10 and stored in a memory thereof, external diagnostic means or a physician, or determined by comparison to a database or look-up table comprising singular values or ranges of values that have been determined to be acceptable and that are stored in microcomputer 58.

Additionally, IMD 10 and microcomputer 58 may be configured to update and change any of the various target pacing rates 620 in response to detected changes in the physiological status of the patient, sensed cardiac or other physiological events occurring in the patient's body, changes made by an attending physician, changing environmental conditions, and so on. Thus, under the control of microcomputer 58 target pacing rate 620 may be changed during time period 600 as required or appropriate.

As seen in FIG. 6, IMD 10 may pace heart 8 at initial pacing rate 630 at start 655 of time period 600. Start time 655 may correspond to the time at which IMD 10 is implanted, may be selected by an attending physician, may be automatically set to commence according to an algorithm stored in a memory of microcomputer 58, may be triggered by the occurrence of a predetermined event sensed by IMD 10, or correspond to the time at which pacing rate function 610 is implemented.

During time period 600, initial pacing rate 630 may be increased during one or more training increments, and the resulting increased pacing rate(s) may also be increased subsequently. In FIG. 6, the slope of pacing rate function 610 between start time 655 and time 665 corresponds to an increase in the pacing rate from initial pacing rate 630 of 50 beats per minute (bpm) to a new pacing rate of 52 bpm over as time period of one day, and thus corresponds to a training increment of 2 beats per minute per day (bpmpd). Other training increments are contemplated in the present invention, including, but not limited to, 0.1 bpmpd, 0.2 bpmpd, 0.3 bpmpd, 0.4 bpmpd, 0.5 bpmpd, 0.6 bpmpd, 0.7 bpmpd, 0.8 bpmpd, 0.9 bpmpd, 1 bpmpd, 1.25 bpmpd, 1.5 bpmpd, 1.75 bpmpd, 2.25 bpmpd, 2.5 bpmpd, 2.75 bpmpd, 3 bpmpd, 4, bpmpd and 5 bpmpd. Consistent with the description given above concerning linear, non-linear, stepwise and other manners of adjusting or controlling the various pacing rates of the present invention, the training increments of the present invention may similarly be adjusted and/or controlled so that heart 8 may be paced in an optimal manner.

Accordingly, pacing rate function 610 may be adjusted and controlled using any suitable means, such as an algorithm stored in a memory of and executed by microcomputer 58, where the algorithm calculates an appropriate training increment by which to increase or decrease pacing rate function 610, or to increase or decrease the training increment. Thus, it is contemplated in the present invention that the training increment be changed from one value to another during time period 600 in accordance with the requirements of the patient, and that the training increment be appropriately increased or decreased during time period 600, again as dictated by patient need. Once time period 600 has been completed, target pacing rate 620 has been attained at end time 685. End time 685 may indicate, for example, the moment at which the time period 600 training period is set to end, or may be the time at which target pacing rate 620 is attained.

Figure 7:
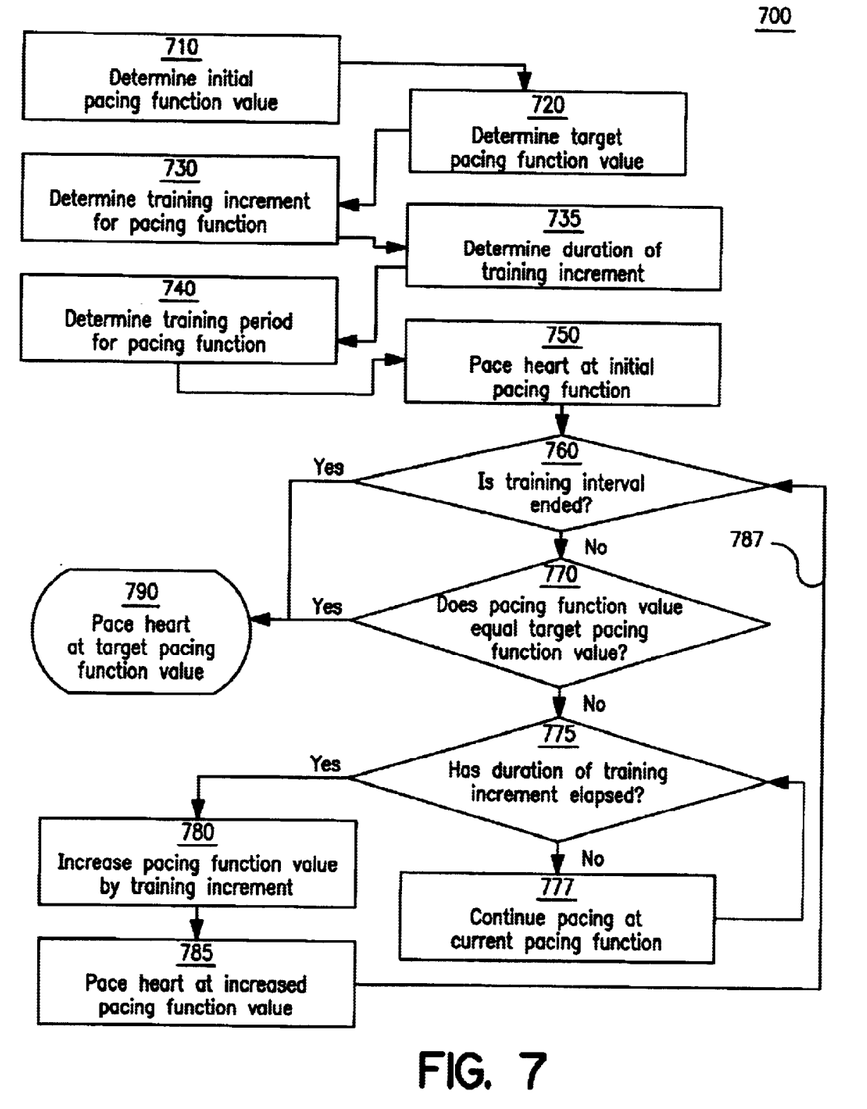
FIG. 7 is a flow diagram of one embodiment of a method for gradual training of a pacing function in accordance with the present invention.

FIG. 7 illustrates one embodiment of a method for training a human heart in accordance with the teachings of the present invention. As discussed above, the method of the present invention may be performed under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64 and/or microcomputer 58.

At block 710 initial pacing rate 630 is determined in accordance with one or more of the methods of determining same described above. For example, initial pacing rate may be a current pacing rate that is measured. Alternatively, initial pacing rate may be set by a physician, selected from a lookup table or database or otherwise determined.

Further in accordance with the methods described above, at block 720 one or more target pacing rates 620 are determined, such as the lower pacing rate limit and the upper pacing rate limit. Alternatively, target pacing rate may be a rate determined in comparison to initial pacing rate 630 for example, by multiplying initial pacing rate 630 by a particular value or percentage, resulting in one or more desired target pacing rates or ranges of target pacing rates.

As seen at block 730, an initial training increment for pacing rate function 610 is set or determined, and may be selected so that initial pacing rate 630 is increased in such a fashion as to permit target pacing rate 620 to be achieved over a predetermined or calculated time period 600. The initial training increment may be based, for example, on the values of the initial and target pacing rate. In one embodiment, for example, the initial pacing rate is subtracted from the target pacing rate and the training increment is an increment of the resulting value.

Also as seen at block 735, a duration corresponding to the initial training increment may also be set by a physician, selected from a look-up table or database, or calculated. In one embodiment of the invention, this duration may be the duration over which the initial pacing rate is incremented to the target pacing rate. Alternatively, this duration may be the duration of a first increment over which initial pacing rate is increased. Thus, the duration may range anywhere between the entirety of time period 600 and some portion or fraction thereof. If the selected initial training increment is less than time period 600, then at least one more training increment must be selected after the initial training increment has expired. Such a subsequent training increment may be set by a physician, selected from a look-up table or database or calculated. In the embodiment of the present invention illustrated in FIG. 6, the duration of the initial training increment is one day. After the initial training increment expires, in FIG. 6 subsequent training increments of one day are implemented.

At block 740, time period 600 over which heart 8 is to be trained is determined. Time period 600 may also be set by a physician, selected from a look-up table or database, or calculated. In one embodiment of the invention, time period 600 may be the duration over which the initial pacing rate is incremented to the target pacing rate. If the selected initial training increment is less than time period 600, then time period 600 may comprise a plurality of training increments described at block 735 above. In the embodiment of the present invention illustrated in FIG. 6, the duration of the initial training increment is ten days and comprises ten one-day increments.

At block 750 heart 8 may be paced at initial pacing rate 630 determined at block 710. In one embodiment of the invention, heart 8 is paced at initial pacing rate for a training increment determined above in order to achieve target pacing rate.

At block 760 it may then be determined if time period 600 has expired and whether target pacing rate 620 has been achieved. If time period 600 has expired, block 790 is proceeded to where heart 8 is paced at target pacing rate 620. Alternatively, heart 8 may be paced at any suitable value once time period 600 has ended.

If at block 760 it is determined that time period 600 has not been completed, block 770 may be proceeded to, where it may be determined if pacing rate function 610 is causing pacing at a rate greater than or equal to target pacing rate 620 determined at block 720. If so, block 790 is proceeded to where heart 8 is paced at target pacing rate 620. Alternatively, heart 8 may be paced at any suitable value once the time period 600 has ended. For example, at point 665 of FIG. 6, the time period 600 has not yet expired and thus, pacing function 610 continues to be adapted in accordance with the present invention.

If pacing rate function 610 causes pacing to be carried out at a rate less than target pacing rate 620, then block 775 is proceeded to. At block 775, it may be determined whether the duration of the initial or other training increment determined at block 735 has elapsed. If the training increment duration has not elapsed, heart 8 may then be paced at the rate then indicated by pacing rate function 610 until the training increment has elapsed (as indicated at 777).

If the training increment duration has elapsed, block 780 may be proceeded to where pacing rate function 610 may be increased by the training increment determined at block 730. At block 785 heart 8 is then paced at the increased pacing rate. For example as seen in FIG. 6, at time period 2 days, heart 8 is paced at an increased pacing rate from the rate shown at time period 1 day.

Block 760 may then be returned to (as indicated at 787) to determine again if time period 600 has expired. If time period 600 has not expired block 770 may be proceeded to, where it may be determined if the increased pacing rate function 610 is causing pacing at a rate greater than or equal to target pacing rate 620 determined at block 720. If so, block 790 is proceeded to where heart 8 is paced at target pacing rate 620. Alternatively, heart 8 may be paced at any suitable value once the time period 600 has ended.

If increased pacing rate function 610 causes pacing to be carried out at a rate less than target pacing rate 620, then block 775 is proceeded to. At block 775, it may be determined whether the duration of the training increment determined at block 735 has elapsed. If the training increment duration has not elapsed, heart 8 may then be paced at the increased pacing rate function determined at 785 until the training increment has elapsed (as indicated at 777).

If the training increment duration has elapsed, block 780 may be proceeded to where increased pacing rate function 610 may again be increased by the training increment determined at block 730. At block 785 heart 8 may then be paced at the new increased pacing rate function. For example as seen in FIG. 6, at time period 3 days, heart 8 is paced at an increased pacing rate from the rate shown at time period 2 days.

The loop indicated at 787 may be repeated until the target pacing function value has been reached. For example, as seen in FIG. 6, the pacing rate is increased from 50 bpm to 70 bpm by a training increment of 2 bmp per day for a total training period of ten days.

In the embodiment of the invention seen in FIG. 7, the parameters determined include: initial pacing function value, target pacing function value, training increment for pacing value; duration of training increment and training period. One or any suitable combination of these parameters may be varied in accordance with the present invention. Alternatively, one or more of these parameters may be set at a desired value while one or more other parameters are varied in accordance with the present invention. Moreover, although the parameters are shown as being determined in a given order, these parameters may be determined in any combination and in any order in accordance with the present invention.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to a method for increasing a pacing parameter of a mammalian heart. The present invention is also not limited to the increase of pacing parameters, per se, but may find further application as a measuring means. The present invention further includes within its scope methods of making and using the measurement means described hereinabove.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

I claim:

1. A method of pacing cardiac tissue using an implantable medical device, comprising:
    implanting the implantable medical device, the implantable medical device having an initial pacing function value based on a current cardiac rate of the cardiac tissue at implantation;
    determining a target pacing function value;
    determining a training increment;
    determining a training period;
    gradually increasing the initial pacing function value to the target pacing function value by to training increment during the training period;
    determining a duration of the training increment;
    increasing the initial pacing function value by the training increment to a first increased value;
    pacing the cardiac tissue at the first increased value for the duration of the training increment; and
    pacing the cardiac tissue at the target pacing function value when the first increased value is equal to the target pacing function value.

2. The method of claim 1, further comprising:
increasing the first increased value by the training increment to a second increased value when the first increased value is not equal to the target pacing function value; and
pacing the cardiac tissue at the second increased value for the duration of the training increment.

3. The method of claim 1, further comprising:
pacing the cardiac tissue at the target pacing function value when the first increased value is greater than the target pacing function value.

4. The method of claim 1 further comprising:
pacing the cardiac tissue at the initial pacing function value.

5. The method of claim 1 further comprising:
pacing the cardiac tissue at the target pacing function value.

6. The method of claim 1 wherein the initial pacing function value is a pacing rate for pacing the cardiac tissue.

7. The method of claim 6 further comprising:
increasing the initial pacing function value by increasing the pacing rate by the training increment.

8. The method of claim 1 further comprising:
increasing the initial pacing function value by decreasing a pacing interval by the training increment.

9. The method of claim 1, further comprising:
determining the initial pacing function value.

10. The method of claim 1, further comprising:
determining the current cardiac rate of the cardiac tissue at implantation.

11. The method of claim 1, further comprising:
setting the initial pacing function value to the current cardiac rate of the cardiac tissue at implantation.

12. The method of claim 1 further comprising:
setting the target pacing function value of the pacing function to a lower limit of a pacing rate of the implantable medical device.

13. The method of claim 1 farther comprising:
setting the target pacing function value of the pacing function is an upper limit of a pacing rate of the implantable medical device.

14. The method as in claim 1, further comprising determining a maximum pacing rate that increases with time and a lower pacing rate that also increases with time.

15. An implantable medical device, comprising:
a processor;
at least one pacing circuit operably connected to the processor wherein,
a heart is paced at an initial pacing function value equal to a current cardiac rate of the heart when the device has been implanted in the heart and the initial pacing function value is gradually increased to a target pacing function value by a training increment over a training period;
at least one pacing electrode for pacing the heart at a first increased value for a training increment duration when the initial pacing function value is increased to the first increased value by the training increment; and
wherein the pacing electrode paces the cardiac tissue at the target pacing function value when the first increased value is equal to the target pacing function value.

16. The device of claim 15 wherein the first increased value is increased to a second increased value by the training increment when the first increased value is not equal to the target pacing function value.

17. The device of claim 15 wherein the pacing electrode paces the cardiac tissue at the target pacing function value when the first increased value is greater than the target pacing function value.

18. The device of claim 15 further comprising:
at least one pacing electrode for pacing the cardiac tissue at the initial pacing function value.

19. The device of claim 15 further comprising:
at least one pacing electrode for pacing the cardiac tissue at the target pacing function value.

20. The device of claim 15 wherein the processor is operatively adapted to increase the initial pacing function value by decreasing a pacing interval based on the training increment.

21. The device of claim 15 wherein the processor is operatively adapted to increase the initial pacing function value by increasing a pacing rate based on the training increment.

22. The device of claim 15, further comprising:
a storage location for storing the initial pacing function value.

23. The device of claim 15, further comprising:
a storage location for storing the target pacing function value.

24. The method as in claim 15 wherein when the initial pacing function value is gradually increased to a target pacing, the gradual increase is performed while staying within a maximum pacing rate that increases with time and a lower pacing rate that also increases with time.

25. A computer usable medium including a program for training a heart with an implantable medical device, comprising:
computer program code that determines an initial pacing function value based on a current cardiac rate at implantation of the implantable medical device;
computer program code that determines a target pacing function value;
computer program code that determines a training increment;
computer program code that determines a training period; and
computer program code that gradually increases the initial pacing function value to the target pacing function value by the training increment during the training period.

26. The program of claim 25, further comprising:
computer program code that determines a duration of the training increment.

27. The program of claim 26, further comprising:
computer program code that increases the initial pacing function value by the training increment to a first increased value; and
computer program code that paces at the first increased value for the duration of the training increment.

28. The program of claim 27, further comprising:
computer program code that increases the first increased value by the training increment to a second increased value when the first increased value is not equal to the target pacing function value; and
computer program code that paces at the second increased value for the duration of the training increment.

29. The program of claim 27, further comprising:
computer program code that paces at the target pacing function value when the first increased value is equal to the target pacing function value.

30. The program of claim 27 further comprising:

computer program code that paces at the target pacing function value when the first increased value is greater than the target pacing function value.

31. The program of claim 25 further comprising:

computer program code that paces at the initial pacing function value.

32. The program of claim 25 further comprising:

computer program code that paces at the target pacing function value.

33. The program of claim 25 further comprising:

computer program code that increases the initial pacing function value by increasing a pacing rate by the training increment.

34. The program of claim 25 further comprising:

computer program code that increases the initial pacing function value by decreasing a pacing interval by the training increment.

35. The program of claim 25, further comprising:

computer program code that determines the current cardiac rate at implantation.

36. The program of claim 25, further comprising:

computer program code that sets the initial pacing function value to the current cardiac rate at implantation.

37. The program of claim 25 further comprising:

computer program code that sets the target pacing function value of the pacing function to a lower limit of a pacing rate of the implantable medical device.

38. The program of claim 25 further comprising:

computer program code that sets the target pacing function value of the pacing function is an upper limit of a pacing rate of the implantable medical device.

39. A method of pacing cardiac tissue using an implantable medical device, comprising:

implanting the implantable medical device, the implantable medical device having an initial pacing function value based on a current cardiac rate of the cardiac tissue at implantation;

determining a target pacing function value;

determining a training increment;

determining a training period; and, gradually increasing the initial pacing function value to the target pacing function value by the training increment during the training period while staying within a maximum pacing rate that increases with time and a lower pacing rate that also increases with time.

* * * * *

UNITED STATES PATENT AND TRADEMARK OFFICE
CERTIFICATE OF CORRECTION

| | | |
|---|---|---|
| PATENT NO. | : 6,650,937 B2 | Page 1 of 1 |
| APPLICATION NO. | : 09/844069 | |
| DATED | : November 18, 2003 | |
| INVENTOR(S) | : Harry B. A. Kerver | |

It is certified that error appears in the above-identified patent and that said Letters Patent is hereby corrected as shown below:

Col. 17, Line 39, delete "1 farther comprising" and insert --1 further comprising--.

Signed and Sealed this

Eleventh Day of July, 2006

JON W. DUDAS
*Director of the United States Patent and Trademark Office*